United States Patent [19]
Hutchison

[11] Patent Number: 5,605,534
[45] Date of Patent: Feb. 25, 1997

[54] SHOWER GUARD FOR IV SITE

[76] Inventor: Jeffrey W. Hutchison, 6143 Lodi Rd., Alexandria, La. 71303

[21] Appl. No.: 579,630

[22] Filed: Dec. 26, 1995

[51] Int. Cl.$^6$ .................................................. A61F 5/00
[52] U.S. Cl. ............................ 602/3; 604/179; 128/849
[58] Field of Search ..................... 602/3, 13; 604/174, 604/177, 179, 180; 128/849, 882

[56] References Cited

U.S. PATENT DOCUMENTS

| | | |
|---|---|---|
| 3,741,203 | 6/1973 | Liman . |
| 3,906,941 | 9/1975 | Cook, Jr. . |
| 4,178,924 | 12/1979 | Baxter .......................................... 602/3 |
| 4,254,765 | 3/1981 | Brown et al. . |
| 4,523,586 | 6/1985 | Couri . |
| 4,610,245 | 9/1986 | Biearman .................................... 602/3 |
| 4,639,945 | 2/1987 | Betz ............................................. 2/22 |
| 5,063,919 | 11/1991 | Silverberg . |
| 5,342,286 | 8/1994 | Kelly et al. .................................. 602/3 |
| 5,395,302 | 3/1995 | Botha et al. ................................. 602/3 |
| 5,415,642 | 5/1995 | Shepherd ............................. 604/180 X |
| 5,449,340 | 9/1995 | Tollini ................................. 602/180 X |

Primary Examiner—Richard J. Apley
Assistant Examiner—Kim M. Lee
Attorney, Agent, or Firm—David L. Ray

[57] ABSTRACT

A protective device or shower guard for covering an IV site having a tube connected thereto to prevent contact of the IV site with water and other contaminants, including a water impermeable, protective sleeve open at one end for placement over the end of the limb and the IV site, a water impermeable flexible band connected to the inside of the sleeve adjacent to the open end of the sleeve, the band extending completely around the inside of the sleeve, the band having a passage extending completely therethrough for receipt of the tube connected to the IV site, a generally rectangular flap formed on the inside of the band adjacent to the passage for selective opening to enable the tube to be placed in the passage, and a seal for sealing the flap to the band after placement of the tube in the passage to prevent liquids from flowing through the band between the flap and the band and through the passage around the outside of the tube. The sleeve preferably has a strap connected to the outside thereof adjacent to the open end of the sleeve between the open end of the sleeve and the band for wrapping around the open end of the sleeve to securely connect the open end of the bag to the limb and prevent the sleeve from sliding on the limb. Furthermore, the sleeve preferably has an accordion-like section between each end of the sleeve which can expand in length.

20 Claims, 2 Drawing Sheets

SHOWER GUARD FOR IV SITE

BACKGROUND OF THE INVENTION

1. Field of the Invention

The invention relates to protective devices for limbs. In particular, the present invention is related to devices for preventing a portion of a limb from getting wet when a person wearing the device is taking a shower.

2. Description of the Related Art

Devices for protecting limbs are known in the art. Some of the protective devices known in the art prevent a portion of a leg or arm from coming into contact with water while bathing or showering.

However, none of the protective devices of the prior art effectively prevent water from contacting an IV site. By IV site is meant the site at which a catheter enters a vein for intravenous transmission of a liquid from a tube into the vein.

When a person has a catheter inserted into the vein of the arm and is receiving fluid through the catheter from a tube connected to a liquid reservoir such as a plastic tube or bottle connected to a stand, if the person desires to take a shower, the IV site may be wrapped with tape, or a plastic bag and tape, in an attempt to prevent water and soap from entering the site and contaminating the site. However, leakage occurs around the tube connected to the catheter where the tube enters the tape or bag. Liquids contacting the IV site can contaminate the site and loosen the bandage or tape holding the catheter to the limb.

Exemplary of the Patents of the related art are the following U.S. Pat. Nos.: 5,395,302; 5,342,286; 5,063,919; 4,639,945; 4,523,586; 4,254,765; 3,906,941; and 3,741,203.

SUMMARY OF THE INVENTION

In accordance with the present invention there is provided a protective device or shower guard for preventing water, soap, and other liquids when showering from contacting an IV site having a tube connected thereto.

The shower guard of the invention includes a water impermeable, protective sleeve open at one end for placement over the end of the limb and the IV site, a water impermeable flexible band connected to the inside of the sleeve adjacent to the open end of the sleeve, the band extending completely around the inside of the sleeve, the band having a passage extending completely therethrough for receipt of the tube connected to the IV site, a generally rectangular flap formed on the inside of the band adjacent to the passage for selective opening to enable the tube to be placed in the passage, and a seal for sealing the flap to the band after placement of the tube in the passage to prevent liquids from flowing through the band between the flap and the band and through the passage around the outside of the tube. The sleeve preferably has a strap connected to the outside thereof adjacent to the open end of the sleeve between the open end of the sleeve and the band for wrapping around the open end of the sleeve to securely connect the open end of the bag to the limb and prevent the sleeve from sliding on the limb. Furthermore, the sleeve preferably has an accordion-like section between each end of the sleeve which can expand in length.

The present invention has the advantage of protecting an IV site from liquids and soap during showering.

The invention has the additional advantage of preventing infection of an IV site during showering.

The invention has the further advantage of enabling a person having an IV site to shower while receiving liquids through a tube connected to the IV site without contamination of the IV site with water and soap.

The invention saves time for the nurse and patient with an IV site during cleaning of the body of the patient by enabling the patient to take a shower with little or no help from a nurse.

The invention has an even further advantage of being low in cost.

DESCRIPTION OF THE PREFERRED EMBODIMENTS

Figure 1:
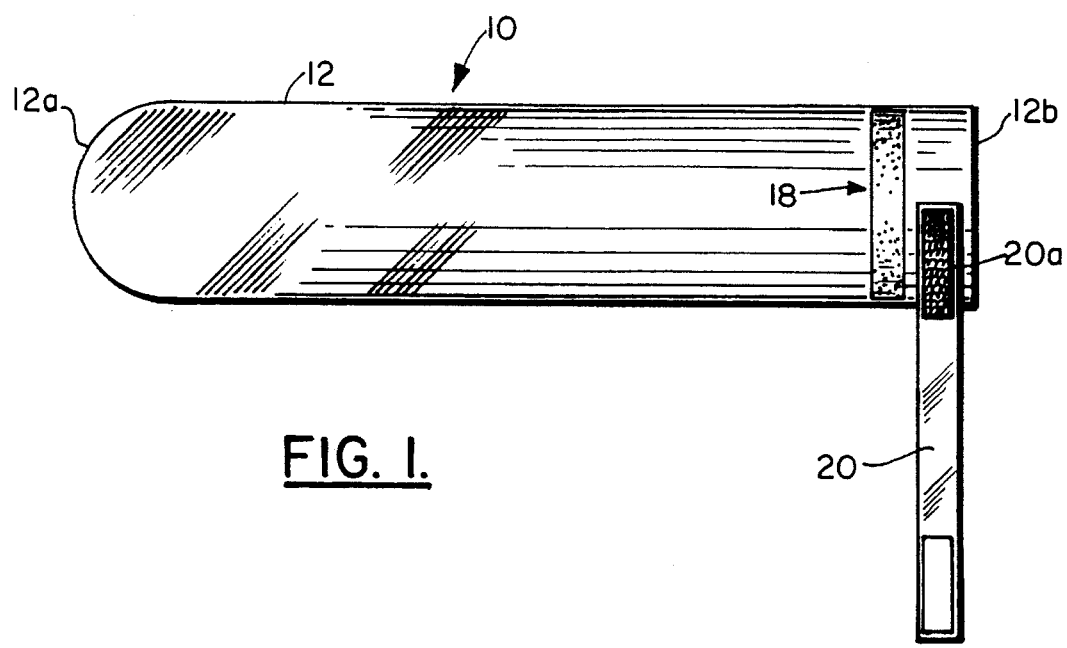
FIG. 1 is a plan view of the shower guard of the invention.
Figure 2:
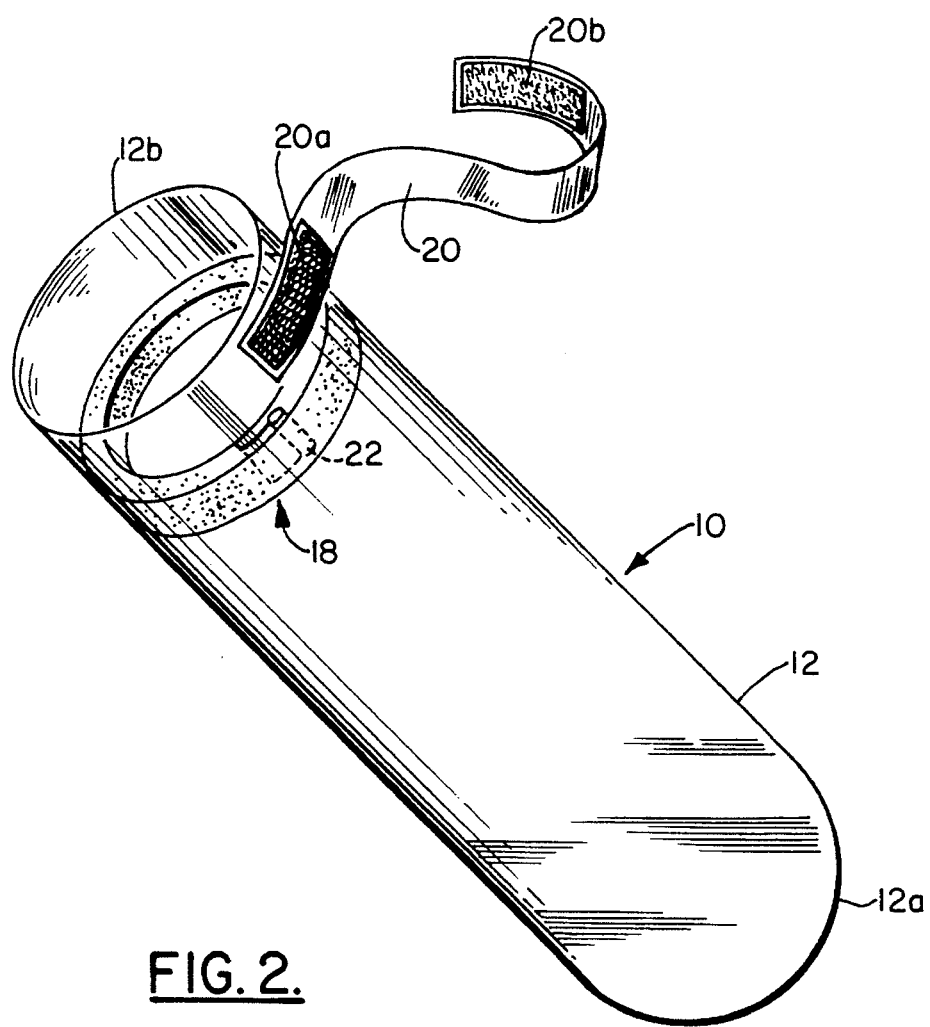
FIG. 2 is a perspective view of the shower guard of the invention.

Referring now to the drawings, in FIG. 1 is shown the shower guard of the invention generally indicated by the numeral 10. Shower guard 10 has a flexible sleeve 12 which is preferably made from a transparent polymeric plastic material such as polyethylene or the like. Sleeve 12 is water-impermeable to prevent wetting of IV site 13 shown in FIG. 4. Sleeve 12 is preferably generally cylindrical in shape with a first closed end 12a and a second open end 12b. The length of sleeve 12 is sufficient to cover the end or hand 14 of limb 16 shown in FIG. 4.

A water-impermeable band generally indicated by the numeral 18 is connected to the inside of sleeve 12 adjacent to open end 12b by gluing, heat-sealing, or any other method known in the art. Preferably band 18 is spaced a distance (preferably about two inches) from the open end 12b of band 18 to enable a strap 20 to be connected to the outside of sleeve 12 between open end 12b and band 18. Band 18 is flexible and is preferably elastic to achieve a snug fit on the limb 16 of the user. If desired, the inside circumference of band 18 may be selected to fit the outside circumference of the portion of limb 16 to which the band is fitted. Preferably band 18 is rectangular in cross-section.

The width of band 18 is selected to prevent liquids from flowing between band 18 and limb 16. Preferably, band 18 is made from a sponge-like polymeric material known to those skilled in the art and sometimes referred to as "sponge rubber". As can be seen in the drawings, band 18 extends continuously completely around the inside of sleeve 12 to prevent water or other liquids from entering the portion of the interior of sleeve 12 between band 18 and closed end 12a.

Figure 3A:
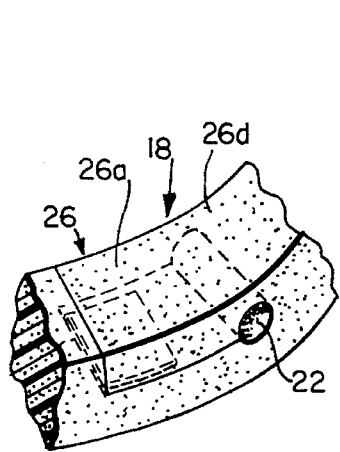
FIG. 3A is a detailed view, partly cross-sectional, of a portion of the shower guard of the invention showing the flap in the closed position.
Figure 3B:
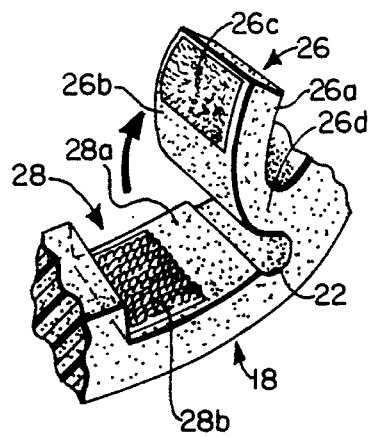
FIG. 3B is a detailed view, partly cross-sectional, of a portion of the shower guard of the invention showing the flap in the open position.
Figure 3C:
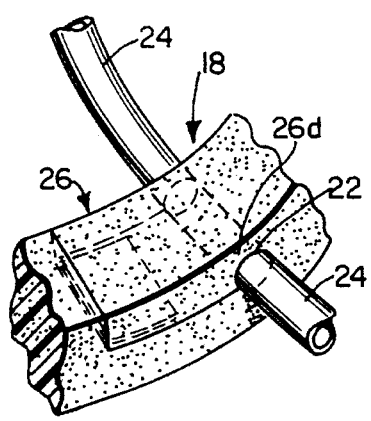
FIG. 3C is a detailed view, partly cross-sectional, of a portion of the shower guard of the invention showing the flap in the closed position with an IV tube extending completely therethrough.

In FIGS. 3A–3C band 18 has a generally cylindrical passage 22 therein for receipt of tube 24. Passage 22 extends completely though the entire width of band 18. The diameter of passage 22 is selected to achieve a snug fit with the outside of tube 24 to prevent water from flowing between the outside of tube 24 and passage 22.

A flap generally indicated by the numeral 26 is preferably integrally formed on the inside of band 18 adjacent to passage 22. Flap 26 is preferably rectangular in cross-section and has an inside face 26a and an outside face 26b which are generally rectangular in shape. Outside face 26b preferably has a seal 26c made from a material such as VELCRO® hook and loop material connected thereto. Band 18 has a recess generally indicated by the numeral 28 which has a generally rectangular inside surface 28a which has a seal 28b made from a material such as VELCRO® connected thereto for selective connection to sealing material 26c to prevent water from flowing therebetween. If the diameter and elasticity of band 18 are selected appropriately, seals 28b and 26c may be omitted and a water resistant seal between flap 26 and surface 26c may be achieved.

Flap 26 is shown in the closed position in FIG. 3A and 3C, and in the open position in FIG. 3B. The portion 26d of flap 26 connects flap 26 to band 18 and acts as a hinge when flap 26 is open as shown in FIG. 3B.

Sleeve 12 preferably has strap 20 connected thereto to prevent sleeve 12 from sliding and moving on the limb 16. If desired, strap 20 could be omitted, and band 18 could be of the appropriate size and elasticity to hold sleeve 12 on limb 16 and prevent water from reaching IV site 13. Furthermore, the open end 12b could be taped to the limb. However, strap 20 is preferred.

Figure 4:
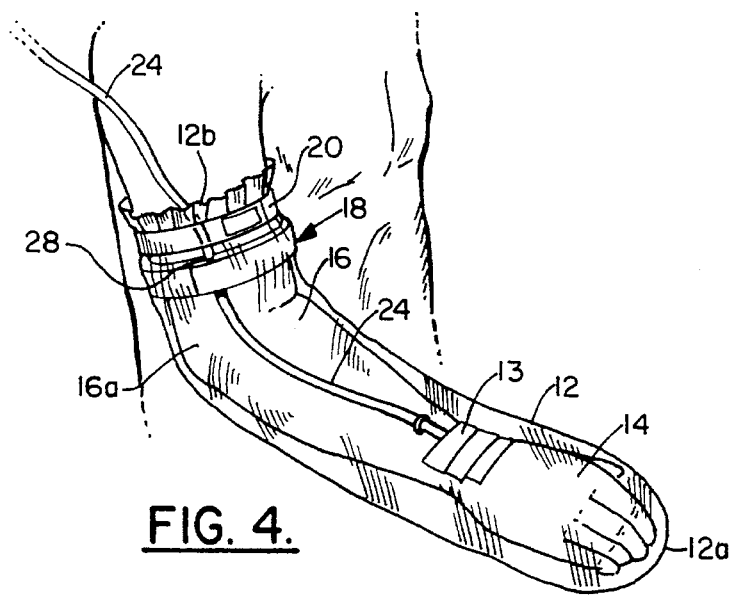
FIG. 4 is a perspective view of the shower guard of the invention connected to the arm of a patient having an IV tube extending through the shower guard to an IV site.

Strap 20 is a generally rectangular strip of flexible plastic or polymeric material which is connected at one end to the outside of sleeve 12 between the open end 12b and band 18. Strap 20 may be connected to sleeve 12 by gluing, heat-sealing, or any other method known in the art. Strap 20 extends completely around the outside surface of sleeve 12. On the outside surface of the portion of strap 20 which is sealed to the outside of sleeve 12 is a generally rectangular seal 20a made from a material such as VELCRO® for connection to seal 20b made from a material such as VELCRO® which is connected to the opposite side of the opposite end of strap 20. Seals 20a and 20b are in alignment for connection when wrapped around limb 16 as shown in FIG. 4. Preferably the length of seals 20a and 20b are sufficient to enable the seals to fit over limbs of various sizes.

Figure 5:
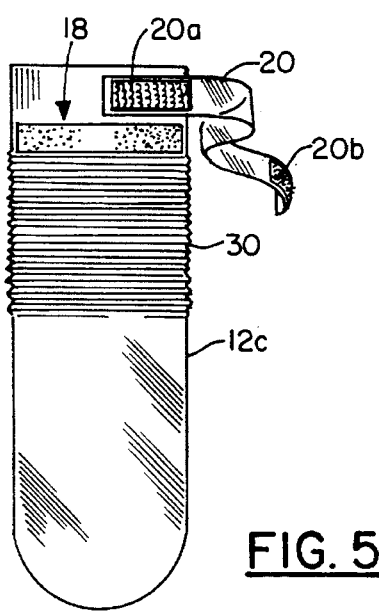
FIG. 5 is a plan view of an alternate embodiment of the shower guard of the invention having a an accordion-like section therein in the folded position.
Figure 6:
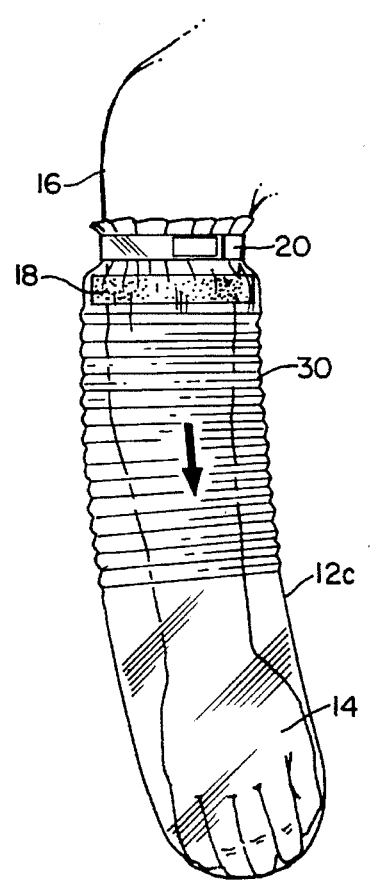
FIG. 6 is a plan view of the shower guard of FIG. 5 connected to an arm with the accordion-like section extended.

In FIGS. 5 and 6 is shown an alternate embodiment of the invention in which sleeve 12c includes a plurality of accordion-like folds 30 formed in sleeve 12c. Folds 30 enable sleeve 12c to extend to various lengths. Sleeve 12c is shown in FIG. 5 in the retracted or folded position in which the overall length of sleeve 12c is the shortest, and in the extended position in FIG. 6. The folds 30 hold the closed end of sleeve 12c against the fingers of the hand 14. Folds 30 thus enable the closed end of sleeve 12a to fit closely against the end of limbs of various lengths.

To place shower guard 10 over an IV site on a limb such as arm 16 having an IV site 13 with tube 24 extending therefrom as shown in FIG. 4, hand 14 is inserted into the open end of sleeve 12 or 12c. The open end 12b, strap 20, and band 18 are preferably positioned above the elbow 16a of arm 16. Flap 26 is opened as shown in FIG. 3B, tube 24 is placed therein, and flap 26 is closed as shown in FIG. 3C. Strap 20 is then extended snugly around the arm 16, and seal 20a is connected to seal 20b. In addition to holding sleeve 12 or 12c on arm 16, strap 20 provides an initial water barrier to protect IV site 13, although some water will flow to band 18 under strap 20 adjacent to tube 24. Band 18 provides a second barrier which prevents all water flow therepast.

Although the preferred embodiments of the invention have been described in detail above, it should be understood that the invention is in no sense limited thereby, and its scope is to be determined by that of the following claims:

What is claimed is:

1. An apparatus adapted to cover an IV site on a limb having a tube connected thereto in order to prevent contact of the IV site with water and other contaminants, the apparatus comprising:

a. a water impermeable sleeve open at one end for placement over the end of said limb and over said IV site, said sleeve having a plurality of folds therein adapted to expand and contract in order to receive limbs of various length, b. a band connected to the inside of said sleeve adjacent to the open end of said sleeve, said band having
      i. a passage formed therein and extending completely therethrough for receipt of said tube connected to said IV site,
      ii. a flap integrally formed on the inside of said band covering said passage for selective opening to enable said tube to be placed in said passage, a portion or said passage being formed in said flap, and
      iii. a seal for sealing said flap to said band after placement of said tube in said passage to prevent liquids from flowing through said band between said flap and said band and through said passage around the outside of said tube.

2. The apparatus of claim 1 wherein said plurality of folds are located adjacent to said band.

3. The apparatus of claim 1 wherein said band is water impermeable.

4. The apparatus of claim 1 wherein said band extends completely around the inside of said sleeve.

5. The apparatus of claim 1 wherein said sleeve has a strap connected thereto for securely connecting said open end of said bag to said limb and preventing said sleeve from sliding on said limb.

6. The apparatus of claim 1 wherein said band is made from sponge rubber.

7. In an apparatus adapted to cover covering an IV site on a limb having a tube connected thereto in order to prevent contact of the IV site with water and other contaminants, the improvement comprising:

a. a water impermeable sleeve open at one end for placement over the end of said limb and over said IV site, b. a water impermeable band connected to the inside of said sleeve adjacent to the open end of said sleeve, said band extending completely around the inside of said sleeve, said band having
      i. a passage formed therein and extending completely therethrough for receipt of said tube connected to said IV site, ii. a flap integrally formed on the inside of said band covering said passage for selective opening to enable said tube to be placed in said passage, a portion of said passage being formed in said flap, and iii. a seal for sealing said flap to said band after placement of said tube in said passage to prevent liquids from flowing through said band between said flap and said band and through said passage around the outside of said tube.

8. The apparatus of claim 7 wherein said band is made from a clear, flexible polymeric material.

9. The apparatus of claim 7 wherein said band is elastic.

10. The apparatus of claim 7 wherein said flap is generally rectangular in shape.

11. The apparatus of claim 7 wherein said sleeve has a strap connected thereto for securely connecting said open end of said bag to said limb and preventing said sleeve from sliding on said limb.

12. The apparatus of claim 11 wherein said strap is connected to the outside of said sleeve adjacent to said open end of said sleeve between said open end of said sleeve and said band for wrapping around said open end of said sleeve.

13. The apparatus of claim 12 wherein said strap is generally rectangular in shape and has two ends.

14. The apparatus of claim 13 wherein said strap has a seal at each end thereof.

15. The apparatus of claim 14 wherein said seal is hook and loop material.

16. The apparatus of claim 15 wherein said seals are connected to opposite sides of said strap.

17. The apparatus of claim 7 wherein said band is made from sponge rubber.

18. The apparatus of claim 7 wherein said band extends completely around the inside of said sleeve, and said band is water impermeable.

19. The apparatus of claim 18 wherein said band is made from a clear, flexible polymeric material.

20. The apparatus of claim 19 wherein said band is elastic.

* * * * *